United States Patent
Doerr et al.

(10) Patent No.: US 8,283,928 B2
(45) Date of Patent: Oct. 9, 2012

(54) METHOD AND ARRANGEMENT FOR DETERMINING A POWER SUPPLY STATE VARIABLE IN AN ACTIVE MEDICAL IMPLANT

(75) Inventors: Thomas Doerr, Berlin (DE); Rainer-Michael Schmidt, Berlin (DE); Peter Blachut, Berlin (DE)

(73) Assignee: BIOTRONIK CRM Patent AG, Baar (CH)

( * ) Notice: Subject to any disclaimer, the term of this patent is extended or adjusted under 35 U.S.C. 154(b) by 343 days.

(21) Appl. No.: 12/701,993

(22) Filed: Feb. 8, 2010

(65) Prior Publication Data

US 2010/0201368 A1    Aug. 12, 2010

(30) Foreign Application Priority Data

Feb. 9, 2009    (DE) .......................... 10 2009 000 728

(51) Int. Cl.
*G01N 27/416* (2006.01)
*A61N 1/00* (2006.01)

(52) U.S. Cl. ............................... 324/427; 607/8; 607/29
(58) Field of Classification Search .................. 324/427; 607/29
See application file for complete search history.

(56) References Cited

U.S. PATENT DOCUMENTS

| | | | |
|---|---|---|---|
| 4,354,148 A * | 10/1982 | Tada et al. ...................... | 320/148 |
| 4,597,037 A * | 6/1986 | Okado ............................. | 363/41 |
| 5,690,685 A | 11/1997 | Kroll et al. | |
| 5,869,970 A | 2/1999 | Palm et al. | |
| 6,028,415 A * | 2/2000 | Nagai et al. .................... | 320/162 |
| 6,940,255 B2 * | 9/2005 | Loch ............................... | 320/132 |
| 2005/0007073 A1 | 1/2005 | James et al. | |
| 2005/0177198 A1 | 8/2005 | Norton et al. | |
| 2008/0097544 A1 | 4/2008 | Gandhi et al. | |

FOREIGN PATENT DOCUMENTS

| | | |
|---|---|---|
| DE | 29 13 399 | 10/1980 |
| DE | 39 01 680 | 3/1990 |
| DE | 197 25 204 | 4/1999 |
| DE | 103 42 633 | 4/2005 |
| EP | 2017757 | 1/2009 |
| WO | 0249718 | 6/2002 |
| WO | 2006107247 | 10/2006 |

OTHER PUBLICATIONS

European Search Report and Written Opinion dated May 27, 2010 (8 pages).
DE 10 2009 000 728.8 German Search Report dated Feb. 2, 2011 (5 pages).

* cited by examiner

*Primary Examiner* — M'Baye Diao
(74) *Attorney, Agent, or Firm* — Buchanan Ingersoll & Rooney PC (57) ABSTRACT

The invention relates to a method and arrangement for determining a power supply state variable, particularly of the maintenance state of a battery or rechargeable battery, in an active medical implant, wherein the power supply is subjected to a predetermined load, and the output voltage thereof is detected multiple times during at least one time segment of the load phase, and the measurement values are subjected to a comparison to a respective comparison value, or the chronological curve of the voltage obtained from the measurement values is subjected to a comparison to at least one comparison curve, wherein the comparison result is considered characteristic for the state variable.

20 Claims, 7 Drawing Sheets

METHOD AND ARRANGEMENT FOR DETERMINING A POWER SUPPLY STATE VARIABLE IN AN ACTIVE MEDICAL IMPLANT

CROSS-REFERENCE TO RELATED APPLICATIONS

This application claims the priority of German Patent Application No. DE 10 2009 000 728.8, filed on Feb. 9, 2009 in the German Patent Office, the disclosure of which is incorporated herein in its entirety by reference.

FIELD OF THE INVENTION

The invention relates to a method for determining a power supply state variable in an active medical implant.

BACKGROUND OF THE INVENTION

The function of active medical implants, particularly of implanted medical-electronic device, decisively depends on the availability of a sufficient operating energy. Since these devices often have a permanent, or in case of an emergency, a vital function for the respective patient, sufficient knowledge on the state of the power supply, particularly of the maintenance state of a batter or rechargeable battery of the implant is indispensable.

The currently known methods of evaluating the battery reliability in ICD is suitable to a very limited degree for identifying problems with batteries early, and thus preventing reliability problems of the ICD. Currently, the battery voltages, the minimum battery voltage during a charging process, and the charging times are being utilized as the criteria for battery monitoring.

All of these measurement values are influenced by environmental factors such that a specific analysis of the battery state is possible only in a very limited manner. The charging time is decisively influenced by the forming state of the impact capacitors. The batter voltage depends on the current operating settings of the ICD (with our without stimulation, etc.). An early detection of problems with the battery is therefore not possibly using the methods stated above. In particular, a so-called voltage delay is only detected, if the battery performance is already irreversibly reduced.

A voltage delay is typical particularly in SVO (silver vanadium dioxide) batteries. In order to avoid the same said batteries are reformed in a non-specific manner. This leads to an unnecessary loss of the charge.

The invention is therefore based on the object of providing a method and an arrangement for the reliable and flexible—with regard to the requirements for realization—determination of a substantial state variable of the power supply of an active medical implant, particularly the maintenance state of the battery or rechargeable battery mentioned. In particular, the early detection of problems with the power supply of an implant—in this regard particularly a so-called voltage delay—is enabled by means of the invention.

SUMMARY OF THE INVENTION

Said problem is solved in the method aspect by means of a method having the characteristics of claim 1, and in the method aspect thereof by means of an arrangement having the characteristics of claim 9. Purposeful further improvements of the novel object of the invention are the object of the respective dependent claims.

The invention includes the idea of subjecting the power supply, specifically the battery or rechargeable battery serving as the energy source, to a predetermined load, and to detect a state-relevant physical variable during at least one time segment. The detection may be carried out continuously, or quasi continuously, or at multiple defined times. In particular, the output voltage of the power supply is detected under the defined load.

The invention further provides that the measurement values taken in accordance with the measuring program, or the chronological curve of the variable derived from the same, are subjected to an evaluation, which is illustrated in the technical sense particularly as a comparison process having corresponding (e.g., comparison measurements taken at respective times) comparison values, or as a comparison of the time dependency with a comparison curve. Such comparison processes are standard procedure today, and corresponding singe value discriminators or sample comparison units are commercially available.

In addition to the higher significance and reliability achieved under possibly undefined conditions as opposed to the singular measurements of the battery voltage, the method provided and the respective arrangement offer flexible options with regard to carrying out the state variable determination, either directly in the implant, or by means of remote monitoring of the same, up to a complex monitoring system for a plurality of implants operated in a large territory.

The realization of the method and of the device in an implantable cardioverter/defibrillator (ICD), wherein the life of the patient depends to the highest degree on the imperative availability of sufficient cardioversion or defibrillation energy in an emergency. Furthermore, the invention may also advantageously be utilized in pacemakers or other implantable tissue stimulators or implantable drug dosing pumps, etc.

In a further embodiment of the invention the same provides that the voltage is quasi continuously detected during the time segment and the time curve is stored completely, or directly transferred, particularly via telemetry, toward the exterior of the implant. As an alternative, the method may be embodied such that the voltage is detected multiple times, particularly at least three times, and preferably at least five times during the time segment, and that the characteristic points or segments of the time segment are determined and stored, or are transferred toward the exterior of the implant, particularly via telemetry.

The determination of the state variable, particularly of the battery parameters, is carried out particularly before and/or during and/or after a capacitor reforming, or also before and/or after the charging process to maximum energy. In a further embodiment of the invention at least three voltage measurements are carried out between the beginning and end of the battery loading. In particular, at least the beginning voltage, the ending voltage, and the consistency of the voltage curve between the beginning and ending voltage are detected between the beginning and end of the battery loading. In particular, at least five voltage values are detected before, during, and after the battery loading per measuring process, and transferred to the remote monitoring system.

The method provided becomes particularly significant, if the measurement values or the chronological curve detected is subjected to a comparison of multiple predetermined comparison values or chronological time curves, and the individual comparison results are subjected to a statistical analysis, wherein the result of the statistical analysis is considered characteristic for the state variable. For this purpose the comparison values, or the comparison time dependencies specifically may be those, which have been detected for comparable devices having comparable energy sources in an operating or maintenance state of varying qualities. Adequate tolerance areas may be defined around characteristic points or chronological measurement value curves (specifically of the voltage) on this basis. Any measuring values or time dependencies outside of the tolerance area are assessed as warnings and may give cause to suitable measures ranging from a recharging or reforming up to an exchange of batteries or devices.

With regard to the specific problem of the voltage delay in certain types of batteries the invention provides in a further embodiment that measurement points of the voltage are determined such that a saw tooth-like decline and renewed increase of the voltage is determined directly after the beginning of the load phase at a sufficient chronological resolution.

The arrangement or system aspects of the invention are largely obvious from the method aspects explained above such that the same will not be illustrated again at this point.

It should be expressly noted, however, that a monitoring system for the monitoring of the state of the power supplies of a plurality of active medical implants may be constructed by means of the arrangements of the type provided. In addition to a plurality of such arrangements the same comprises a monitoring server for detecting and storing the initial variables supplied by the analysis units of the arrangements in association with a respective implant, and optionally of data further present in the analysis units, as well as for processing the same for the central monitoring and optional operating control of the implants related to the system, and a plurality of relay stations associated with one or multiple analysis units for the data transfer between the analysis units and the monitoring server, particularly via a mobile communications network.

BRIEF DESCRIPTION OF THE DRAWINGS

The advantages and utilities of the invention are obvious by way of the following description of exemplary embodiments based on the figures. They show.

DETAILED DESCRIPTION OF THE INVENTION

Figure 1:
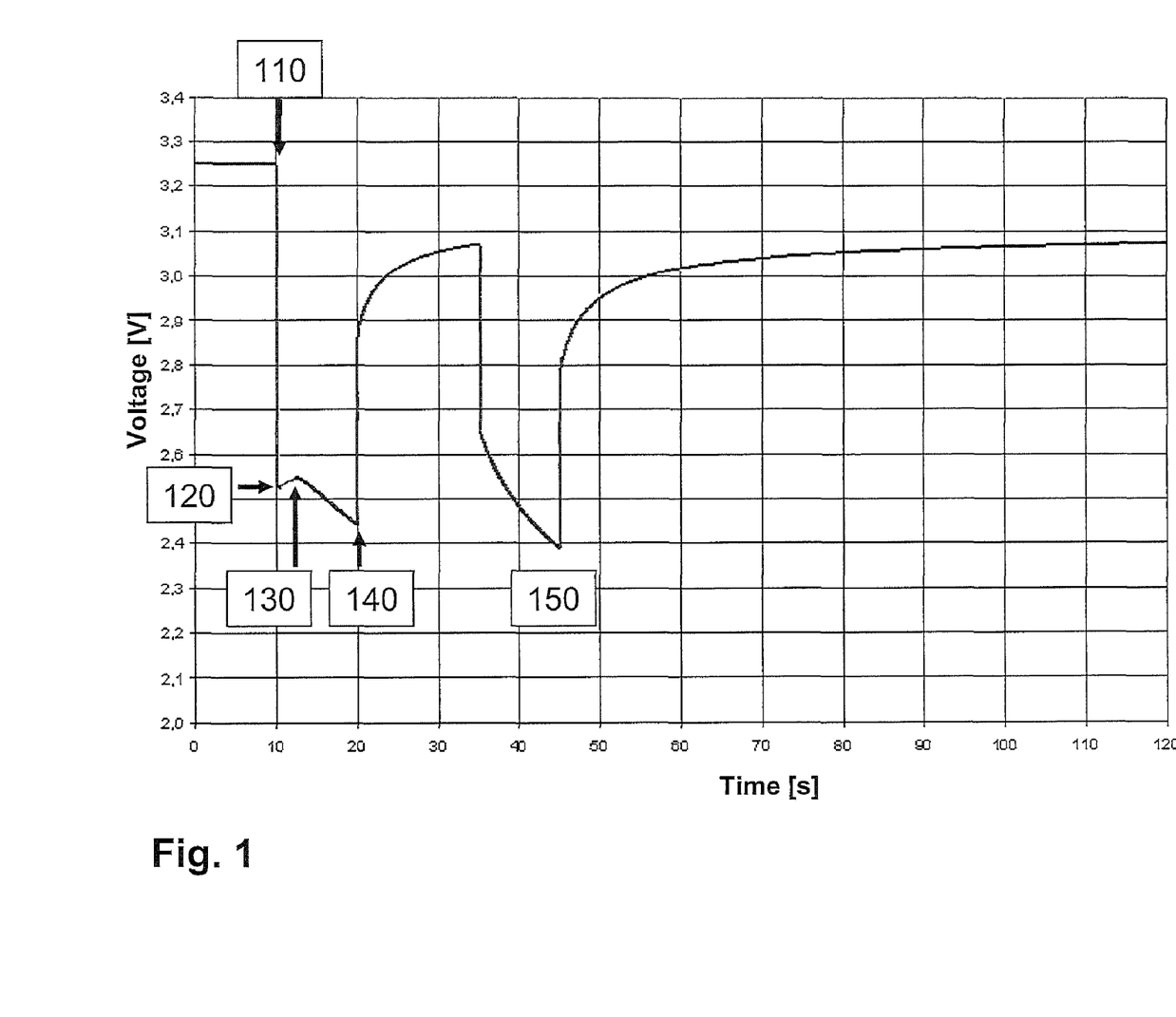
FIGS. 1 and 2 are graphical illustrations of the chronological curve of the battery voltage of an active implant at a defined load.

FIG. 1 shows the battery voltage curve of an ICD battery during two successive charging processes. Due to the voltage drop at the interior resistance of the battery, but also due to electro-chemical processes (dynamic interior resistance), the open-circuit voltage 110 breaks into an initial value (12) at the beginning of the charging process. A slight voltage increase 130 initially occurs during the first charging process due to chemical processes (reforming) within the battery. Said voltage increase is an expression of a slight "voltage delay" and may be considered normal after long storage, for example in SVO batteries. In this case the ending voltage is significantly below the initial value 120.

The second charging process (the beginning denoted with 150) shows a completely normal voltage curve having a steady decrease of the battery voltage during battery loading.

Figure 2:
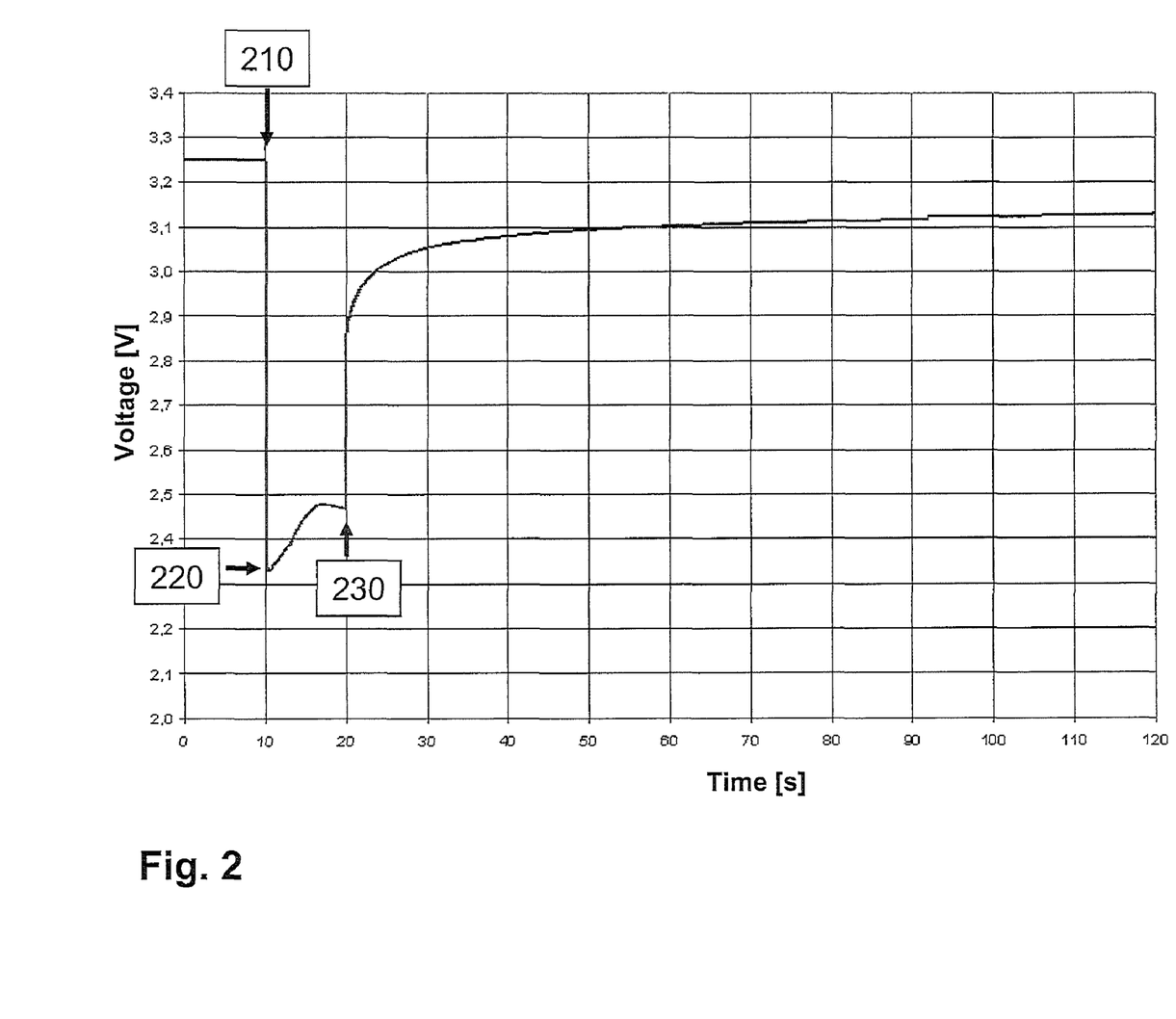

FIG. 2 shows the battery voltage curve of an ICD battery having a pronounced "voltage delay." Based on the unremarkable open-circuit voltage 210 of the battery the voltage breaks down to an untypically low initial value 220 at the beginning of the charging process, and then increases during the charging process. The final value 230 in this case is at the same level as with a normal charging process, and is significantly above the initial value.

The voltage delay shown in the example would not be uniquely identifiable by way of the charging time, since the reforming effect of the battery is still being effectively completed during the charging process. However, such a voltage curve is a distinct indicator for a pronounced voltage delay providing an indication as to an increased reforming requirement. In this case it would be necessary to significantly shorten the reforming interval of the ICD; otherwise a premature battery drain would be the result.

Figure 3:
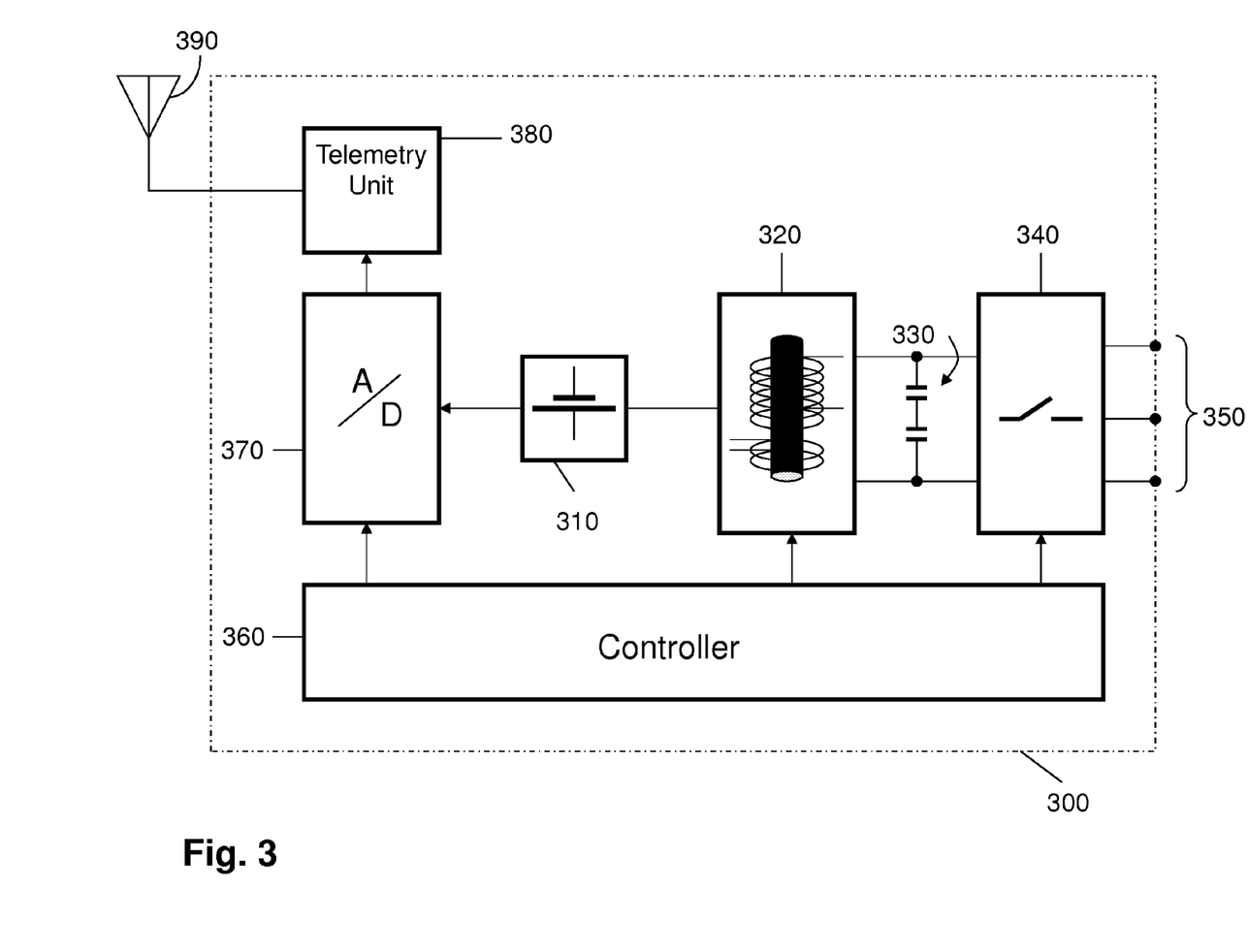
FIG. 3 is a schematic illustration of essential components of an arrangement according to the invention in an implantable defibrillator.

FIG. 3 shows the block diagram of an implantable defibrillator (ICD) 300. The same has a battery 310, which supplies, among others, the charging circuit for the initial shock stage 340 that forwards the shock energy to the defibrillation electrodes 350, if necessary. The control of the charging processes and of the shock output control is carried out by means of a controller 360. Said controller 360 also controls the battery monitoring unit 370 which is connected to the battery such that the measurement of the battery voltage is enabled at defined times before, during, and after the charging process.

The measurement values of the battery monitoring unit are provided to the telemetry unit 380 after completion of the measurement. Said telemetry unit 380 operates within the MICS or GSM band, and is connected to a remote monitoring system via a respective antenna 390 for the purpose of data transfer.

Figure 4:
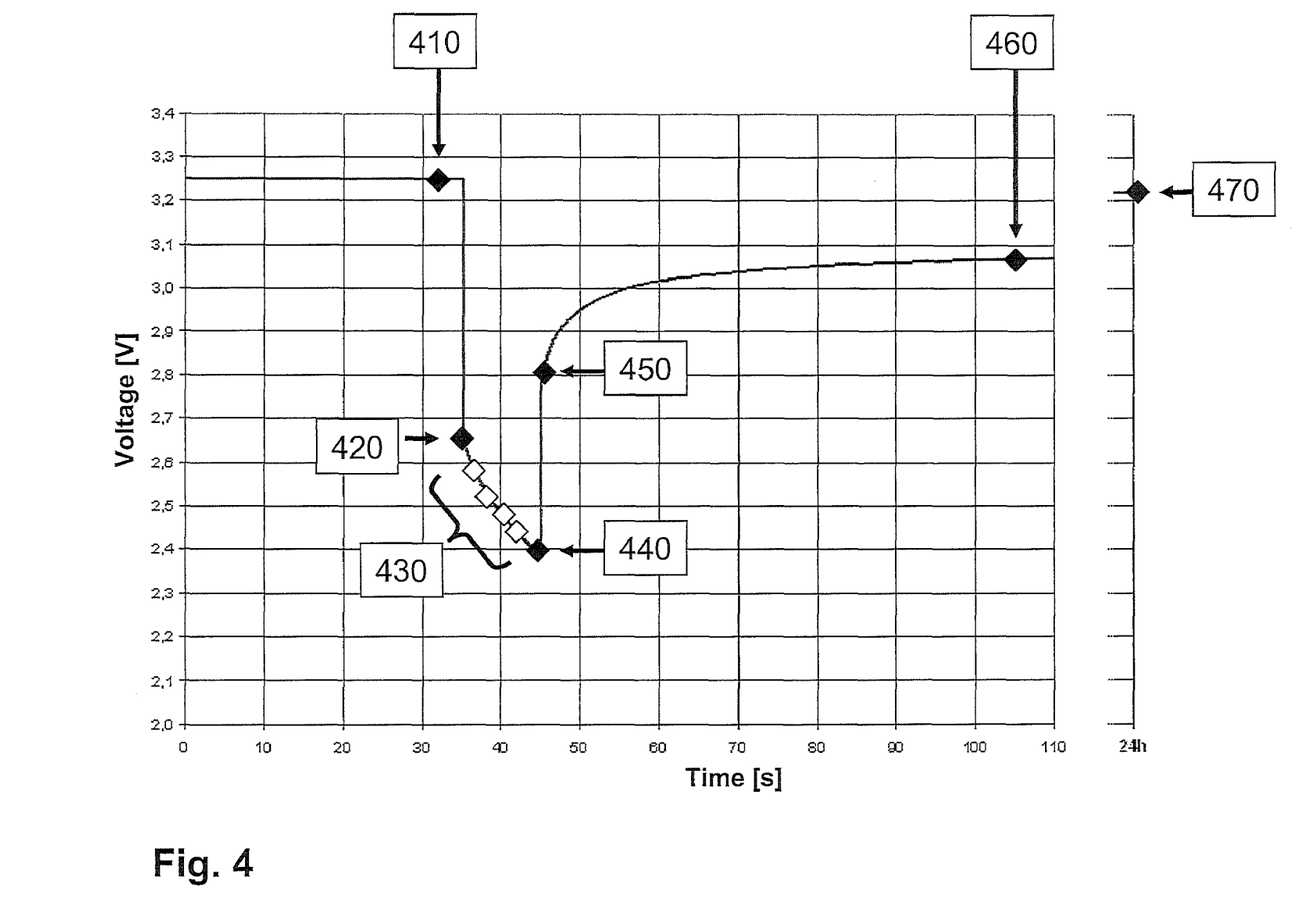
FIG. 4 is a graphical illustration as to the carrying out of the method according to the invention based on a further battery voltage curve.

FIG. 4 shows points in time of the battery voltage measurement that are selected in a meaningful manner during and after a capacitor reforming. The controller 360 illustrated in FIG. 3 causes the battery monitoring unit 370 to a series of battery voltage measurements whenever an automatic capacitor reforming is carried out. The carrying out of the measurements based on a capacitor reforming provides the advantage that the same is carried out in chronologically uniform intervals (i.e., every 3 months), and a defined charging process (start: capacitor voltage=0V; end capacitor voltage=maximum charging voltage) is always carried out.

A first voltage measurement is carried out directly before the beginning of the charging process 410, a second measurement is carried out directly after switching on the charging circuit (420). Subsequently, measurements are carried out every 10-100 ms at a consistent chronological interval (430) until the charging end has been reached. The last measurement value before charging end (440) is denoted as such. Directly before switching off the charging circuit a further measurement (450) is carried out. The last measurement of this series of measurements is carried out 24 hrs after the end of the capacitor reforming.

Figure 5:
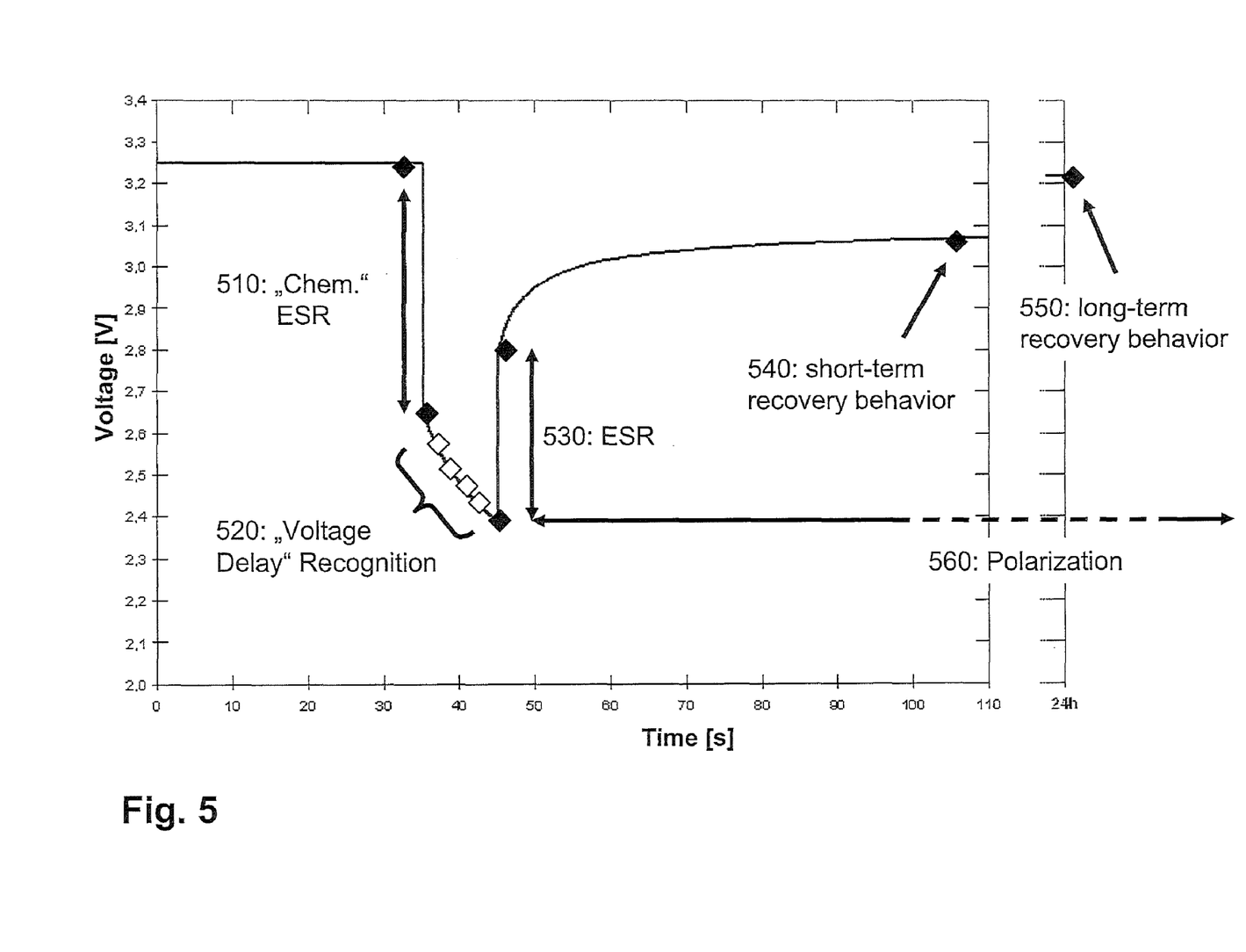
FIG. 5 is a schematic illustration for explaining the method according to the invention based on the battery voltage curves according to FIG. 4.

FIG. 5 shows which battery variables may be determined using the solution according to the invention. The difference of the open-circuit voltage and the initial voltage of the charging process indicate the so-called "chemical" interior resistance 510 of the battery.

The recording of the voltage curve during the charging process 520 serves for recognizing a beginning or pronounced "voltage delay." If the measurement values are consistent, and if the initial voltage is above the end voltage, no voltage delay is present. If the end voltage is above the initial voltage, a pronounced voltage delay is present.

The voltage difference of the end voltage of the charging process and the voltage measured directly after switching off the charging circuit corresponds to the interior resistance (530: ESR) of the battery. The comparison thereof to the "Chem. ESR" 510 additionally allows conclusions as to the stability of the electro-chemical system of the battery.

The battery voltage measured one minute after the end of the charging process is an expression of the short-term recovery behavior 540 of the battery. This value represents the properties of the battery of being able to operate multiple charging processes in short intervals (i.e. in case of shock series).

The battery voltage 550 measured after 24 hours describes the long-term recovery behavior of the battery. At this time the recovery of the battery voltage is completed after a charging process. This value may be utilized as an additional exchanging criterion for the battery.

Figure 6:
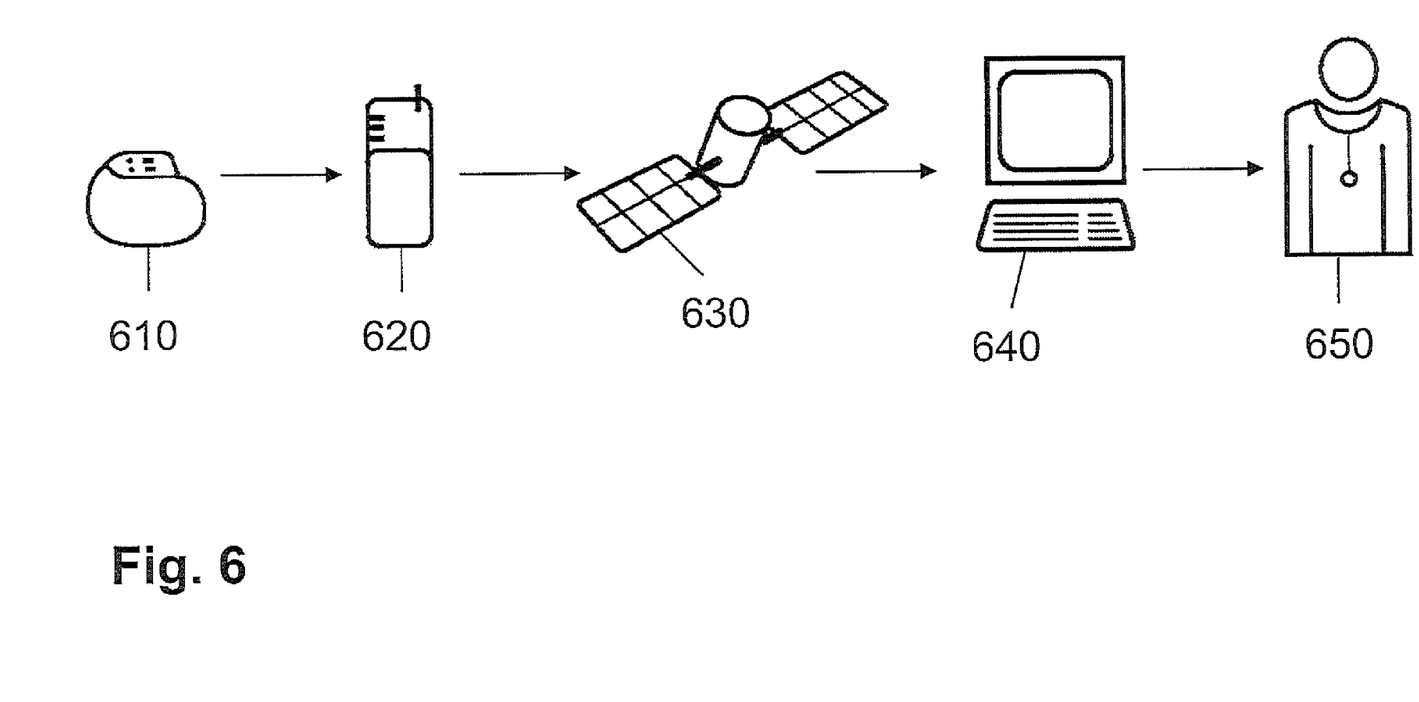
FIG. 6 is a schematic illustration of a monitoring system according to the invention.

The illustration 6 schematically illustrates an implant monitoring system utilizing the battery voltage values. An implant 610 transmits messages to a relay station 620 in regular intervals. The MICS band and a so-called patient device, or as an alternative the GSM band and a GSM base station, are preferably utilized for the data transfer. A relay station 620 subsequently transfers the data via a network 630 to a remote monitoring server 620, and provides the data of the battery diagnostics to the doctor/user in a processed form. For this purpose the processing is preferably carried out in a format the user is familiar with, such as a display BOL, MOL, ERI/RRT, or EOS.

The illustration in FIG. 6 is greatly simplified stark; of course, in practice the illustrated system will comprise a plurality of implants, as well as a plurality of associated relay stations, and a plurality of computer workstation of different doctors will in turn be connected to the monitoring server, which are responsible for the care of one or multiple patients having active implants, and which utilize the obtained measurement values processed in the system.

Figure 7:
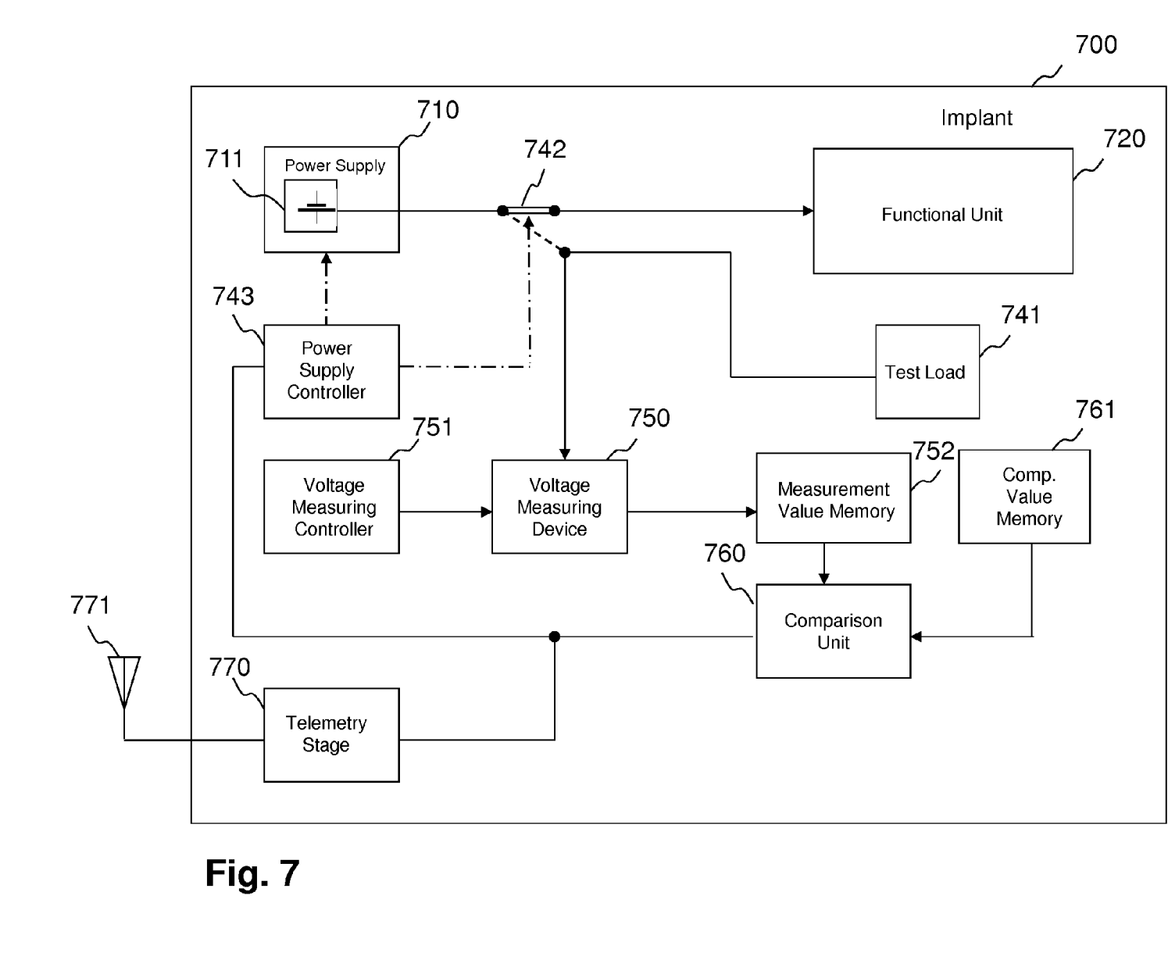
FIG. 7 is a schematic illustration of a further embodiment of the arrangement according to the invention.

FIG. 7 shows essential components of a further active medical implant 700 in the context of the invention, namely initially a power supply 710 having a rechargeable battery 711 as the energy source, for operating a functional unit 720, such as a stimulation impulse generator, a drug dosing pump, or the like. Furthermore, a special test load 741 is provided in this embodiment, by means of which the rechargeable battery 711 is connected via a switch 742 for carrying out a state testing measurement series, which in turn is operated by a power supply controller 743.

In the switching state of the power supply 710 being connected to the load 741 the output voltage thereof is tapped at predetermined time intervals via a voltage measuring device 750 under the control of a voltage measuring controller 751 according to a measurement program stored therein, and the measurement values detected are stored in a measurement value memory 752. The stored measurement values are fed to an input of a comparison unit 760, the other input of which is connected to a comparison value memory 761, and receives relevant comparison values (or also a stored comparison time curve) from there. The initial values of the comparison unit 760 characterizing the comparison result are returned to the power supply controller 743 in order to be utilized as an input signal for determining and carrying out suitable processes depending on the state detected (as far as possible within the implant).

Simultaneously the comparison result of a telemetry stage 770 is fed using an antenna 771 toward the exterior of the implant for transmission in order to supply the comparison result to the responsible doctor, thus supplying a statement on the state of the rechargeable battery 711. The doctor may then make a decision on any measures necessary, which require an exercise of control on the implant, such as a recharging or optionally an exchange of the rechargeable battery. The type of external devices which may be utilized for this purpose is known to the person skilled in the art, and therefore does not require any further explanation.

The carrying out of the invention is not limited to the examples and high-lighted aspects of the invention described above, but is possible in a plurality of variations that are within the scope of the actions of a person skilled in the art.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

We claim:

1. A method for determining a power supply state variable for the maintenance state of a battery or a rechargeable battery in a medical implant, the method comprising the steps of:
    subjecting a power supply to a predetermined load;
    detecting measurement values of an output voltage of the power supply at multiple times during at least one time segment of a load phase;
    either:
        subjecting the measurement values to a comparison having a respective comparison value; and/or
        subjecting a chronological curve of the output voltage obtained from the measurement values to a comparison to at least one comparison curve; and
    considering the results of the comparison a characteristic for the power supply state variable.

2. The method according to claim 1, wherein the output voltage is quasi continuously detected during the at least one time segment, and the time curve is either completely stored or directly transferred to the exterior of the implant.

3. The method according to claim 2, wherein the time curve is directly transferred to the exterior of the implant via telemetry.

4. The method according to claim 1, wherein the output voltage is detected between approximately 3-5 times during the at least one time segment, and wherein characteristic points or segments of the time curve determined from the measurement values of the output voltage are stored or are transferred toward the exterior of the implant.

5. The method according to claim 4, wherein the characteristic points or segments of the time curve determined from the measurement values of the output voltage transferred toward the exterior of the implant via telemetry.

6. The method according to claim 1, wherein at least one measurement value of the output voltage is detected after the beginning and before the end of the load phase, and other measurement values of the output voltage are detected before and/or after the load phase.

7. The method according to claim 1, wherein the determination of the state variable is carried out before, during and/or after a reforming of an energy storage capacitor of the implant.

8. The method according to claim 1, wherein the determination of the state variable is carried out before, during and/or after a process of charging an energy storage capacitor of the implant to maximum energy.

9. The method according to claim 1, wherein the measurement values detected or the chronological curve obtained from the measurement values are subjected to a comparison to multiple predetermined comparison values or chronological curves, and the individual comparison results are subjected to a statistical analysis, wherein the result of the statistical analysis is considered a characteristic for the power supply state variable.

10. The method according to claim 1, wherein the measurement values of the output voltage are determined such that a saw tooth-like decline and renewed increase of the voltage is determined directly after the beginning of the load phase at a sufficient chronological resolution.

11. An arrangement for carrying out a method for determining a power supply state variable for the maintenance state of a battery or a rechargeable battery in a medical implant, wherein the power supply is subjected to a predetermined load, and measurement values of an output voltage thereof are detected at multiple times during at least one time segment of a load phase, and either the measurement values are subjected to a comparison having a respective comparison value, and/or a chronological curve of the output voltage obtained from the measurement values is subjected to a comparison to at least one comparison curve, and wherein the comparison result is considered a characteristic for the power supply state variable, the arrangement comprising:
- a power supply controller for initiating and ending a load phase of a power supply of the implant at a predetermined load;
- a voltage measuring device for measuring measurement values of an output voltage of the power supply;
- a voltage measuring controller for the chronological controlling of the voltage measuring device such that measurement values are detected at predetermined times;
- a comparison memory for storing comparison values of the output voltage and/or a comparison time curve; and
- a comparison unit for (a) comparison of the measurement values obtained at certain times to respective comparison values, and/or (b) comparison of a chronological curve composed of the measurement values to the comparison time curve, and for obtaining an initial variable characterizing the comparison result, wherein the initial variable is considered a characteristic for the power supply state variable.

12. The arrangement according to claim 11, embodied as an integral part of an active medical implant.

13. The arrangement according to claim 12, wherein the active medical implant comprises an implantable cardioverter/defibrillator.

14. The arrangement according to claim 11, wherein the power supply controller, the voltage measuring device, and the voltage measuring controller are embodied as integral parts of an active medical implant, wherein the arrangement further comprises a transmission device for transferring the detected measurement values toward the exterior of the implant, and wherein remaining components of the arrangement are arranged outside of the implant and includes a receiving device for receiving the measurement values sent by the implant.

15. The arrangement according to claim 14, wherein the transmission and receiving devices comprise telemetry devices.

16. The arrangement according to claim 14, wherein the active medical implant comprises an implantable cardioverter/defibrillator.

17. The arrangement according to claim 14, further comprising an analysis device embodied for the communication with a plurality of active medical implants and for the ordered storing and comparison analysis of measurement values, which are sent by said implants.

18. The arrangement according to claim 17, wherein a statistics analysis step is conducted downstream of the comparison device in the analysis device, which is embodied for the analysis of the measurement values sent by multiple implants, and the output of the statistics analysis step is connected to a transmission device of the analysis device for transferring an initial signal characteristic for the result of the statistical analysis to a receiving device of the implant, and wherein the receiving device of the implant is connected to an input of the power supply controller for transferring the signals received thereto.

19. The arrangement according to claim 11, wherein the power supply controller is connected to the comparison unit on the input side for receiving the initial variable and is embodied such that a load or reforming or similar operating process is carried out in the power supply as a function of the initial variable.

20. A monitoring system for the monitoring of the state of power supplies of a plurality of active medical implants, having a plurality of arrangements according to claim 12, the monitoring system comprising:
- a monitoring server for detecting and storing the initial variables supplied by the analysis devices of the arrangement in association with an implant, and optionally further data present in the analysis devices, the monitoring server processing the initial variables and optional further data for the central monitoring and the optional operating control of the implants related to the system; and
- a plurality of relay stations associated to one or multiple analysis devices for the data transfer between the analysis devices and the monitoring server via a mobile communication network.

* * * * *